United States Patent
Li (10) Patent No.: US 6,180,348 B1
(45) Date of Patent: Jan. 30, 2001

(54) METHOD OF ISOLATING TARGET SPECIFIC OLIGONUCLEOTIDE LIGANDS

(76) Inventor: Weihua Li, 12647 Caminito, San Diego, CA (US) 92130

(*) Notice: Under 35 U.S.C. 154(b), the term of this patent shall be extended for 0 days.

(21) Appl. No.: 09/287,936

(22) Filed: Apr. 7, 1999

Related U.S. Application Data (60) Provisional application No. 60/082,405, filed on Apr. 20, 1998.

(51) Int. Cl.[7] .................... C12Q 1/68; G01N 33/53; C07H 21/04; C07H 21/00
(52) U.S. Cl. .................... 435/6; 435/7.1; 536/23.1; 536/24.3; 536/25.32
(58) Field of Search .................. 435/6, 7.1; 536/23.1, 536/24.3, 25.32

(56) References Cited

U.S. PATENT DOCUMENTS

| | | | |
|---|---|---|---|
| 5,362,866 | 11/1994 | Arnold, Jr. ................ | 536/25.3 |
| 5,475,096 | 12/1995 | Gold et al. ................ | 435/6 |
| 5,487,973 | * 1/1996 | Nilsen et al. ............. | 435/6 |
| 5,582,981 | 12/1996 | Toole et al. .............. | 536/23.1 |
| 5,595,877 | 1/1997 | Gold et al. ................ | 435/6 |
| 5,660,985 | 8/1997 | Pieken et al. ............. | 435/6 |
| 5,756,291 | * 5/1998 | Griffin et al. ............. | 435/6 |

FOREIGN PATENT DOCUMENTS

| | | |
|---|---|---|
| WO 94/14843 | 9/1992 | (WO) . |
| WO 94/02515 | 2/1994 | (WO) . |

OTHER PUBLICATIONS

Bruno, J.G. Biochemical and Biophysical Research Communication 234, 117–120 (1997).*

Tuerk, Craig and Larry Gold, "Systematic Evolution of Ligands by Exponential Enrichment: RNA Ligands to Bacteriophage T4 DNA Polymerase," *Science*, 249:505–510 (1990).

Bock, Louis C. et al., "Selection of single–stranded DNA molecules that bind and inhibit human thrombin," *Nature*, 355:564–566 (1992).

Conrad, Richard C. et al., "In Vitro Selection of Nucleic Acid Aptamers That Bind Proteins," *Methods in Enzymol.*, 267:336–367 (1996).

O'Reilly, Michael S. et al., "Endostatin: An Endogenous Inhibitor of Angiogenesis and Tumor Growth," *Cell*, 88:277–285 (1997).

Schmidtmayerova, Helena et al., "Human immunodeficiency virus type 1 infection alters chemokine β peptide expression in human monocytes: Implications for recruitment of leukocytes into brain and lymph nodes," *Proc. Natl. Acad. Sci., USA*, 93:700–704 (1996).

Yoshikawa, Toshikazu et al., "A Novel Cancer Therapy Based on Oxygen Radicals," *Cancer Research*, 55(8):1617–1620 (1995).

Ho, David D., "Toward HIV Eradication or Remission: The Tasks Ahead," *Science*, 280:1866–1867 (1998).

Papadopulos–Eleopulos et al., "Factor VIII, HIV and AIDS in haemophiliacs: an analysis of their relationship," *Genetica*, 95:25–50 (1990).

Jones, A. L. et al., "Haemostatic changes and thromboembolic risk during tamoxifen therapy in normal women," *Br. J. Cancer*, 66:744–747 (1992).

Griffin, John H. et al., "Anticoagulant Protein C Pathway Defective in Majority of Thrombophilic Patients," *Blood*, 82:1989–93 (1993).

(List continued on next page.)

*Primary Examiner*—George C. Elliott
*Assistant Examiner*—Mark L. Shibuya
(74) *Attorney, Agent, or Firm*—Lyon & Lyon LLP (57) ABSTRACT

This invention relates to methods of preparing oligonucleotide libraries, isolating oligonucleotide aptamers to target molecules from the libraries, and using the aptamers to purify target molecules by affinity separation. Specific oligonucleotide aptamers to erythropoietin were isolated accordingly.

13 Claims, 6 Drawing Sheets

OTHER PUBLICATIONS

Davis, Heather L. et al., "Direct gene transfer in skeletal muscle: plasmid DNA–based immunization against the hepatitis B virus surface antigen," *Vaccine*, 12:1503–1509 (1994).

Maskos, Uwe and Edwin M. Southern, "Oligonucleotide hybridisations on glass supports: a novel linker for oligonucleotide synthesis and hybridisation properties of oligonucleotides synthesised in situ," *Nucleic Acid Research*, 20:1679–1684 (1992).

McCollum, Christie and Alex Andrus, "An Optimized Polystyrene Support For Rapid, Efficient Oligonucleotide Synthesis," *Tetrahedron Letters*, 32:4069–4072 (1991).

Gao, Hetian et al., "H–Phosphonate Oligonucleotide Synthesis On a Polyethylene Glycol/Polystyrene Copolymer," *Tetrahedron Letters*, 32:5477–5480 (1991).

Crea, Roberto and Thomas Horn, "Synthesis of oligonucleotides on cellulose by a phosphotriester method," *Nucleic Acid Research*, 8:2331–2348 (1980).

Pon, Richard T., "Solid–Phase Supports for Oligonucleotide Synthesis," *Methods in Molecular Biology*, 20:465–496 (1993).

Gallop, Mark A. et al., "Applications of Combinatorial Technologies to Drug Discovery," *Journal of Medicinal Chemistry*, 37:1233–1251 (1994).

Gold, Larry, "Oligonucleotides as Research, Diagnostic, and Therapeutic Agents," *The Journal of Biological Chemistry*, 270:13581–4 (1995).

Huang, Shao–Chie et al., "Binding of Biotinylated DNA to Streptavidin–Coated Polystyrene Latex," *Analytical Biochemistry*, 222:441–449 (1994).

Fry, G. et al., "A New Approach to Template Purification for Sequencing Applications Using Paramagnetic Particles," *BioTechniques*, 13:124–131 (1992).

Gutterman, Jordan U., "Cytokine therapeutics: Lessons from interferon α," *Proc. Natl. Acad. Sci.*, 91:1198–1205 (1994).

Nicola, Nicos A., "Hemopoietic Cell Growth Factors and Their Receptors," *Annu. Rev. Biochem.*, 58:45–77 (1989).

Howard, O. M. Zack et al., "Chemokines: progress toward identifying molecular targets for therapeutic agents," *Trends in Biotechnology*, 14:46–51 (1996).

* cited by examiner

Diagram of using magnetic force to separate oligonucleotide ligand with desired affinity to target Magnetic Separation Oligonucleotide ligand library

Magnetic bead with immobilized target molecules

Fig. 1

Diagram of using fluorescent activated sorting to separate oligonucleotide ligand with desired affinity to target Fluorescent activated sorting Oligonucleotide ligand library ⛬ Fluorescent probe tagged target molecule

GROUP I

Consensus    TGTTTGTT
F18  GGCCATCGTTCCTGTTCCTTATCTTCAATACGCTGCCGCGACCTT
F15  GGGGGCCAAGGATTCATGTGTTGTTAACAGCTAGCGCCGCTT
F21  GGGACCTCCCAGAAGCGAAGGTGTTCAACGTTGGTTTAGGTTT
F22  GGGACAAGGTTGTAGGCTTCAGTGTCTCTGTTCGTGTTGGTT
F17  GGCGATACGGAATATTGGTACCACCTATGTGTAGATGTTTGTT

GROUP II

F8   GGCCCGGTTGGTGAGATCAGAGTTAGTGAGTTCTCTGTCCGTT
F13  GGGAGCCGAATGTATGAAAGTGCTGAGTACAGGTGCTCGGGGGTT
F19  GGGGCAGGGGCGGACGACGGCTAGTGCAGACTTTTGGTGGGTT

Oligonucleotide ligands that bound to Erythropoietin

Fig. 4

Binding of Ligand F15 to Erythropoietin

Fig. 5

Purification of Prothrombin with Oligonucleotide Ligand

Fig. 6

METHOD OF ISOLATING TARGET SPECIFIC OLIGONUCLEOTIDE LIGANDS

RELATED APPLICATIONS

This application claims the benefit of priority under 35 U.S.C. 119(e) to U.S. provisional application U.S. Ser. No. 60/082,405, filed Apr. 20, 1998, the contents of which, including drawings and sequence, are hereby incorporated by reference into the present application.

FIELD OF THE INVENTION

The present invention relates to the synthesis and identification of oligonucleotide ligands of target molecules and uses thereof. The invention also relates to Fluorescence Activated Cell Sorter analysis, i.e., FACScan flow cytometetry, and other convenient separation means.

BACKGROUND OF THE INVENTION

SELEX, i.e., Systematic Evolution of Ligands by Exponential Enrichment, is a process of isolating oligonucleotide ligands of a chosen target molecule (see Tuerk and Gold, *Science* 249:505–510, (1990), U.S. Pat. Nos. 5,475,096, 5,595,877, and 5,660,985). SELEX as described in Tuerk and Gold involves admixing the target molecule with a pool of oligonucleotides (e.g., RNA) of diverse sequences; retaining complexes formed between the target and oligonucleotides; recovering the oligonucleotides bound to the target; reverse-transcribing the RNA into DNA; amplifying the DNA with polymerase chain reactions (PCR); transcribing the amplified DNA into RNA; and repeating the cycle with ever increasing binding stringency. Three enzymatic reactions are required for each cycle. It usually takes many cycles (e.g., between 12–15 cycles) to isolate aptamers of high affinity and specificity to the target. An aptamer is an oligonucleotide that is capable of binding to an intended target substance but not other molecules under the same conditions.

Bock et al., (1990) *Nature* 355:564–566, describes another approach of isolating aptamers. Bock's process is different from that of Tuerk and Gold in that only one enzymatic reaction is required for each cycle (i.e., PCR) because the nucleic acid library in Bock's method is comprised of DNA instead of RNA. The identification and isolation of aptamers of high specificity and affinity with the method of Bock et al. still requires repeated cycles in a chromatographic column.

Conrad et al., (1996) *Methods in Enzymol.* 267:336–367, describes a variety of methods for isolating aptamers, all of which employ repeated cycles to enrich target-bound ligands and require a large amount of purified target molecules.

SUMMARY OF THE INVENTION

The present invention features a simple, speedy and cost efficient method of identifying aptamers to specific target molecules. It allows for the identification and isolation of aptamers without numerous cycles of selection and amplification.

Within the scope of this invention, Applicant successfully identified and isolated synthetic single-stranded oligonucleotides of high affinity to a target molecule of interest, erythropoietin. In addition, Applicant successfully used a synthetic single-stranded oligonucleotide in an affinity matrix to purify another molecule of interest, prothrombin. The Applicant's success in these endeavors suggests a broad-spectrum applicability of the invention that is not limited to the specific biologic molecules studied herein. Those of skill in the art will appreciate that such can be applied to any molecule or compound of interest, biologic or otherwise, that has an affinity for oligonucleotide ligand sequences of the type described herein.

In a first aspect, this invention features a method that makes use of magnetic separation to identify an aptamer which specifically binds to a target molecule of interest by magnetic separation. In this method, the target molecule is conjugated to a magnetic substance. After allowing the target molecule to mix with a collection of candidate oligonucleotides under conditions suitable for complex formation, i.e., binding of target molecule with aptamer(s), magnetic force is applied to separate aptamer(s) from the rest of the candidate oligonucleotides that have little or no affinity for the target molecule. Preferably, this method contains the following steps:

a) providing a collection of candidate oligonucleotides attached to a plurality of solid supports, wherein candidate oligonucleotides of different nucleotide sequences are attached to different solid supports and all candidate oligonucleotides attached to a single solid support are of the same nucleotide sequence;

b) providing a plurality of magnetic beads covered with the target molecule;

c) admixing the collection of candidate oligonucleotides on solid supports with the magnetic beads covered with the target molecule under conditions suitable for the binding of oligonucleotide ligands to the target molecule, wherein magnetic bead conjugates complex with one or more solid supports bearing aptamers to the target molecule of interest;

d) applying magnetic force to isolate one or more solid supports attached with magnetic beads; and e) identifying oligonucleotides present on the isolated solid supports.

A collection of candidate oligonucleotides is generated using conventional synthesis techniques. Preferably, each oligonucleotide in the collection contains both a randomized sequence as well as at least one adjacent primer sequence for amplification and/or sequencing. Candidate oligonucleotides include single-stranded and double-stranded RNA or DNA of any length. A candidate oligonucleotide may contain modified or derivatized groups known in the art, especially those identified in U.S. Pat. Nos. 5,582,981 and 5,660,985, such as analogous forms of purines and pyrimidines and analogous forms of ribose and deoxyribose.

Figure 4:
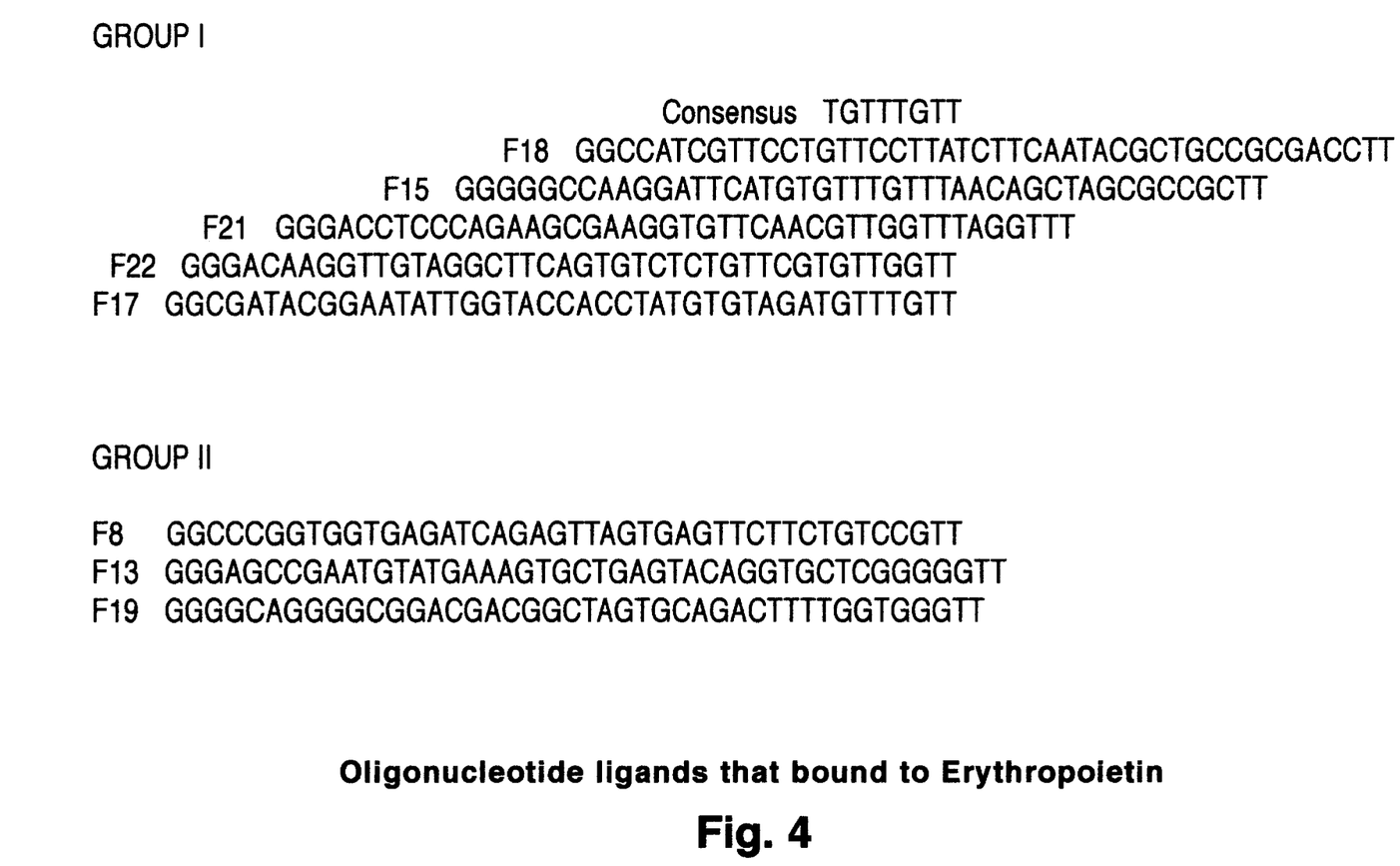
FIG. 4 is a diagram showing the sequences of aptamers to erythropoietin which are isolated from an oligonucleotide library. A consensus sequence is identified in the aptamers of Group I. Group II is comprised of oligonucleotides not containing the consensus sequence.
Figure 5:
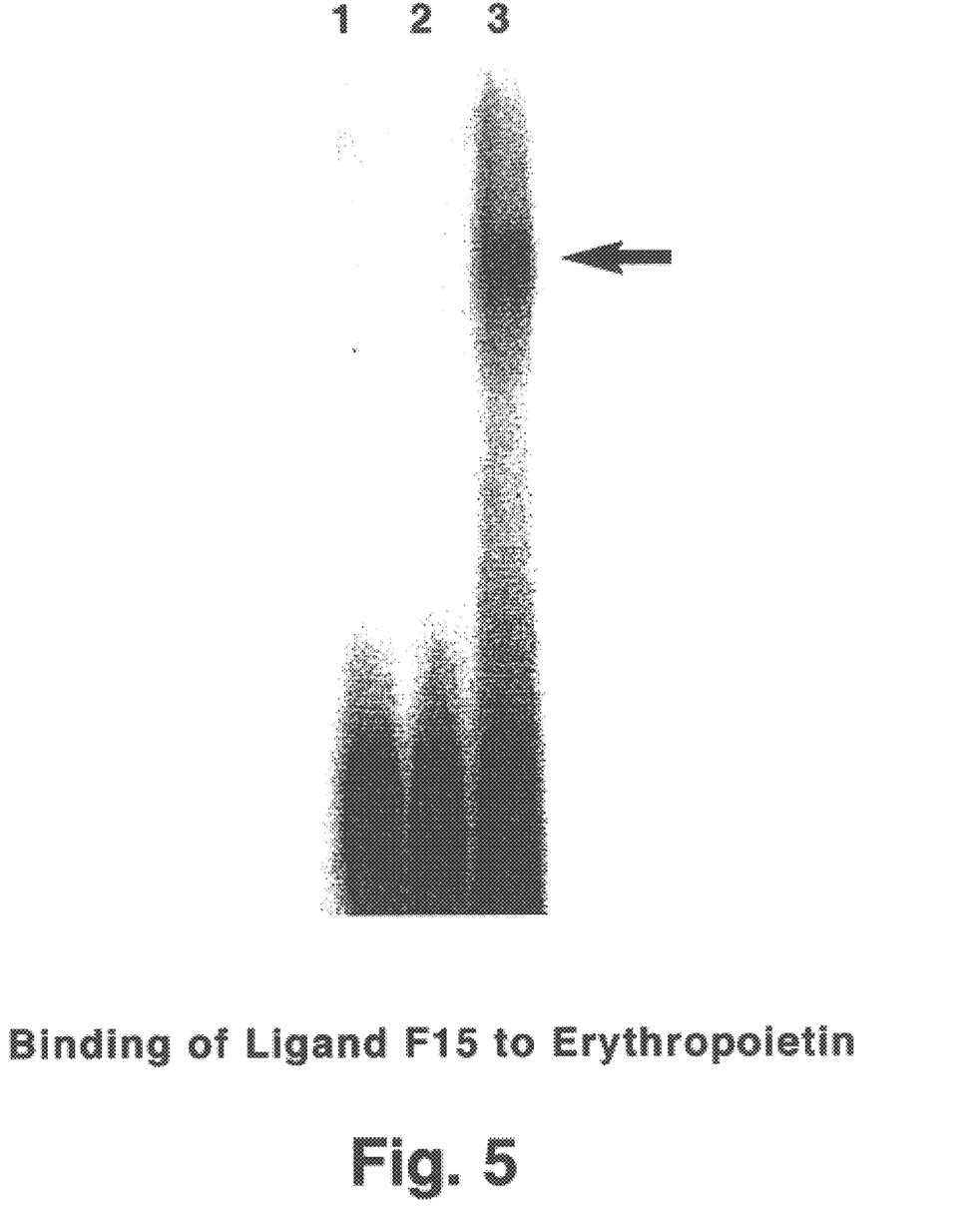
FIG. 5 is an autoradiogram showing the specific binding of an isolated oligonucleotide, F15 (Seq ID No: 9), to erythropoietin in native polyacrylamide gel electrophoresis. It also shows that oligonucleotide F15 does not bind to the negative control, i.e., an equal amount of bovine serum albumin.
Figure 6:
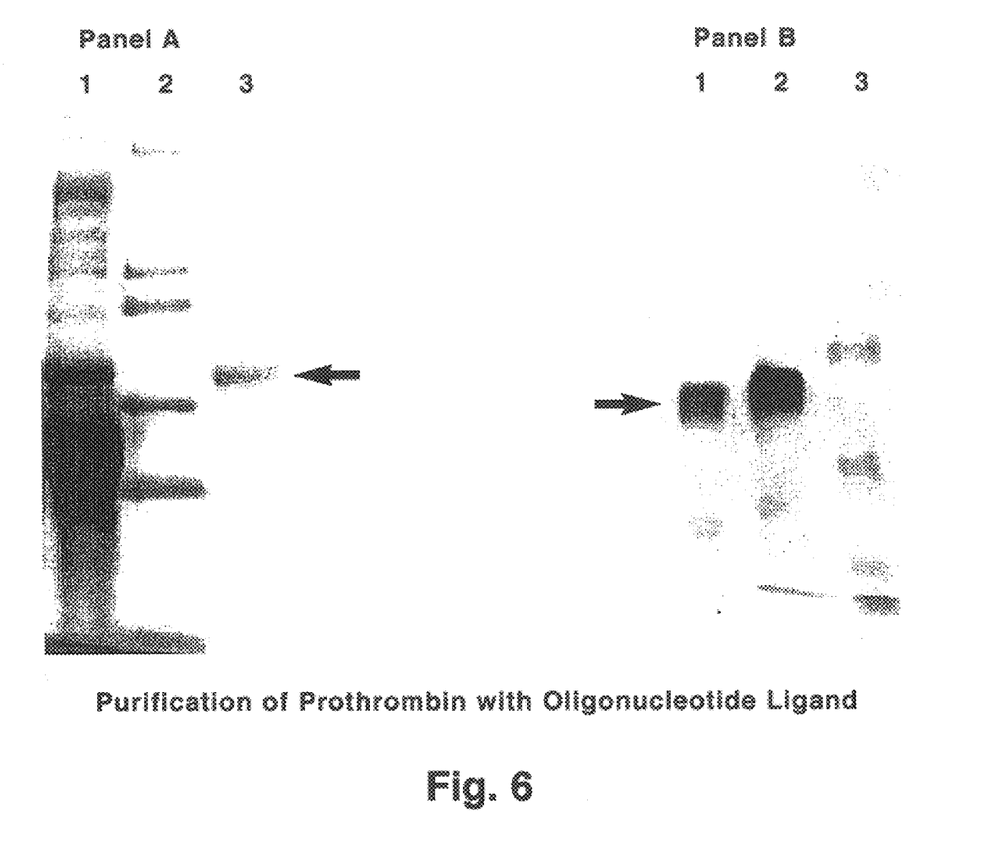
FIGS. 6A and 6B comprises two radiograms verifying the purification of prothrombin with an oligonucleotide ligand matrix.

In FIG. 4, the oligonucleotides shown correspond to the sequence listing as follows: F18 is SEQ ID NO. 8; F15 is SEQ ID NO. 9; F21 is SEQ ID NO. 10; F22 is SEQ ID NO. 11; F17 is SEQ ID NO. 12; F8 is SEQ ID NO. 13; F13 is SEQ ID NO. 14; and F19 is SEQ ID NO. 15.

A target molecule can be any molecule capable of forming a complex with an oligonucleotide, including, but not limited to, peptides, proteins, enzymes, antibodies, hormones, glycoproteins, polymers, polysaccharides, nucleic acids, small organic compounds such as drugs, dyes, metabolites, cofactors, transition state analogs and toxins.

Specific target molecules of interest include molecules of biological and physiological relevance in both prokaryotic and eukaryotic organisms, particularly mammals. Examples of such biologically significant molecules in mammals include, but are not limited to, erythropoietin, tissue plasminogen activator, granular colony stimulating factor (G-CSF), growth hormone (GH), endostatin (O'Reilly et al., (1997) *Cell* 88:277–285), interferons, interleukins, chemokines (Shi et al., (1997) *FASEB J*. 11:1330; Bubrovsky et al., (1996) *PNAS, USA* 92:700–709), enzymes such as SOD (Yoshikai et al., (1995) *Cancer Res*. 55(8) 1617–1620) and amylase, antibodies (particularly the constant "Fc" regions thereof), OKT3 (Ho et al., (1998) *Science* 280:1866–1867), serum proteins (e.g., Factor VIII (Papadopulos-Eleopulos et al., (1990) *Genetica* 95:35–50), Factor VIX, plasminogen, antithrombin III (Jones et al., (1992) *Br. J. Cancer* 66:744–747), albumin, protein C (Griffin et al., (1993) *Blood* 82:1989–93), etc.), and vaccines (e.q., HbsAg (Davis et al., (1994) *Vaccine* 12:1503–1509), etc.). The physiological significance of most of these, and many other molecules, may similarly be found in Goodman and Gilman's *The Pharmacological Basis of Therapeutics*, $8^{th}$ ed., (1990) Pergamon Press, Elmsford, N.Y. Those of skill in the art will appreciate that a virtually unlimited number of other target molecules may also be used with the claimed methods.

The solid support can be anything suitable for attaching oligonucleotides, including, but not limited to, resin beads, controlled pore glass (e.g., Maskos and Southern, (1992) *Nucleic Acid Res*. 20:1679–1684), polystyrene (e.g., McCollum and Andrus, (1991) *Tetrahedron Lett*. 32:4069–4072), PEG-polystyrene (e.g., Gao et al., (1991) Tetrahedron Lett. 32:5477–5480), Teflon (e.g., Arnold, U.S. Pat. No. 5,362,866), cellulose (e.g., Crea and Horn, (1980) Nucleic Acid Res. 8:2331–2348). In a preferred embodiment, the oligonucleotides of diverse sequences are synthesized on the solid supports (e.g., Pon, (1993) *Methods Mol. Biol*. 20:465–496). In another preferred embodiment, the solid support is of a size observable under an optical microscope. Such a size facilitates the selection of individual solid supports following magnetic separation. Oligonucleotides attached to individual solid supports can be sequenced directly to obtain the identity, consensus sequence and/or structure information of the aptamers. Preferably, the solid support has a diameter of about 50 um to about 500 um, more preferably about 70 um to about 150 um, and even more preferably about 90 um to about 120 um. The target molecule is optionally labeled with a fluorescent label to facilitate the identificcation and selection of solid supports which form complexes with the target molecule through aptamer/target molecule interaction.

The magnetic beads covered with the target molecule are preferably much smaller than the solid supports attached with oligonucleotides. For example, the magnetic beads may have a diameter of about 1 um to about 10 um, or about 2 um to about 5 um.

If too many solid supports are selected by the above described process, one can increase the binding stringency and isolate a more limited set of solid supports attached with oligonucleotides of higher affinity to the target molecule. If none or too few solid supports are selected by the process, one can lower the binding stringency to isolate more solid supports. The phenomenon of stringency is known by those of skill in the art to be routinely affected and modulated by parameters such as temperature and ion strength of solution.

In a second aspect, this invention features a method of identifying an aptamer which specifically binds to a target molecule by fluorescence activated sorting. In this method, the target molecule contains or is attached with a fluorescent label. After allowing the target molecule to mix with a collection of candidate oligonucleotides under conditions suitable for aptamer binding and complexing, fluorescence activated sorting is applied to separate aptamer(s) complexed with the fluorescent target molecule from the rest of the candidate oligonucleotides. Preferably, this method contains the following steps:

a) providing a collection of candidate oligonucleotides attached to a plurality of solid supports, wherein candidate oligonucleotides of different nucleotide sequences are attached to different solid supports, each support having identical oligonucleotide sequences bound thereto;

b) providing fluorescence labeled target molecules;

c) admixing the candidate oligonucleotides on solid supports with the target molecules under conditions suitable for oligonucleotide/target molecule binding;

d) isolating one or more solid supports attached with the fluorescence labeled target molecules; and e) identifying oligonucleotides attached to the isolated solid supports.

In a preferred embodiment, the solid supports attached with the fluorescence labeled target molecules are isolated by fluorescence activated sorting. Because FACscan can sort particles into different fractions according to their fluorescence intensity, this method allows a series of oligonucleotides to be sorted according to relative affinity strength to target molecule, i.e., solid supports bearing higher affinity oligonucleotides attract more fluorescence labeled target molecules.

In another preferred embodiment, the fluorescence labeled target molecules are linked to magnetic beads and magnetic separation is applied before the florescence activated sorting. This step increases the speed of FACscan by reducing the number of particles to be sorted.

In a third aspect, this invention features a method of identifying an aptamer which specifically binds to a target molecule. This method contains the following steps:

a) providing a collection of oligonucleotides of diverse sequences in a liquid, wherein each of said oligonucleotides is linked with a detectable label such as a fluorescent label;

b) attaching a plurality of solid supports, e.g., resin beads, to target molecules, said target molecules exposed on the support surfaces and accessible to olignonucleotides;

c) admixing the collection of oligonucleotides with the solid supports covered with the target molecule under conditions suitable for oligonucleotide binding to the target molecule;

d) selecting solid supports linked to fluorescence labeled oligonucleotides by fluorescence activated sorting; and e) identifying the oligonucleotides linked to the selected solid supports, e.g., by amplification and sequencing.

By utilizing magnetic separation and/or fluorescence activated sorting, the processes of this invention allow the isolation and identification of an aptamer in a single step without repeated cycles. The processes described above for isolating aptamers may be used in lieu of or in combination with conventional methods in the art, including, but not limited to, those described in U.S. Pat. Nos. 5,475,096 and 5,582,981.

Following the identification of aptamers with the processes described in this application, one can further delineate consensus secondary structures and primary sequences, tertiary structures, motifs, and activity boundaries using methods known in the art, including, but not limited to, those described in U.S. Pat. No. 5,595,877. Nucleic acid ligands, once identified, can be further modified or derivatized using methods known in the art, including, but not limited to, those described in U.S. Pat. No. 5,660,985.

In an example, oligonucleotides that specifically bind to erythropoietin were isolated and identified with a method of this invention. Specifically, the present invention provides single stranded DNA ligands to erythropoietin according to the method described above. The sequences of these ligands are listed in FIG. 4. Also included is consensus DNA sequence identified by sequence homology and binding ability to erythropoietin. Thus, in another aspect, this invention features an oligonucleotide aptamer binding to erythropoietin with an affinity of no less than $10^{-4}$ M. The affinity ranges from $10^{-3}$ to $10^{-8}$ M, preferably $10^{-6}$ to $10^{-8}$ M.

In a preferred embodiment, the oligonucleotide aptamer is substantially homologous, preferably no less than 70%, more preferably no less than 80%, and even more preferably no less than 90%, to the sequences of FIG. 4. Homology is defined as identical bases at the same position within the range of sequence nucleotide positions that is compared. Preferably, the homology is from about 75% to about 100% within the 8 base consensus region in FIG. 4, Group I. In another preferred embodiment, such an oligonucleotide aptamer to erythropoietin contains a sequence as shown in FIG. 4.

Oligonucleotides designed to closely resemble or match the consensus sequence would have high affinity for the target molecule. For example, an oligonucleotide containing multiple consensus sequences separated by spacers would have high affinity for the target molecule. Specifically, an oligonucleotide containing two consensus regions linked by a 6 base spacer binds to erythropoietin as strong as F15.

Other features and advantages of the invention will be apparent from the following drawings and detailed description of the invention and from the claims.

BRIEF DESCRIPTION OF THE DRAWINGS

(A): Collected fractions on 7.5% SDS-PAGE of. Lane 1, crude human plasma; lane 2, molecular weight marker (BioRad, low range); lane 3, wash fraction; lane 4, eluted prothrombin fraction.

(B): Western blot analysis of collected fractions. Molecular weight and prothrombin positions are marked by arrows.

DETAILED DESCRIPTION OF THE INVENTION

1. Selecting Aptamers by Magnetic Bead Separation

Figure 1:
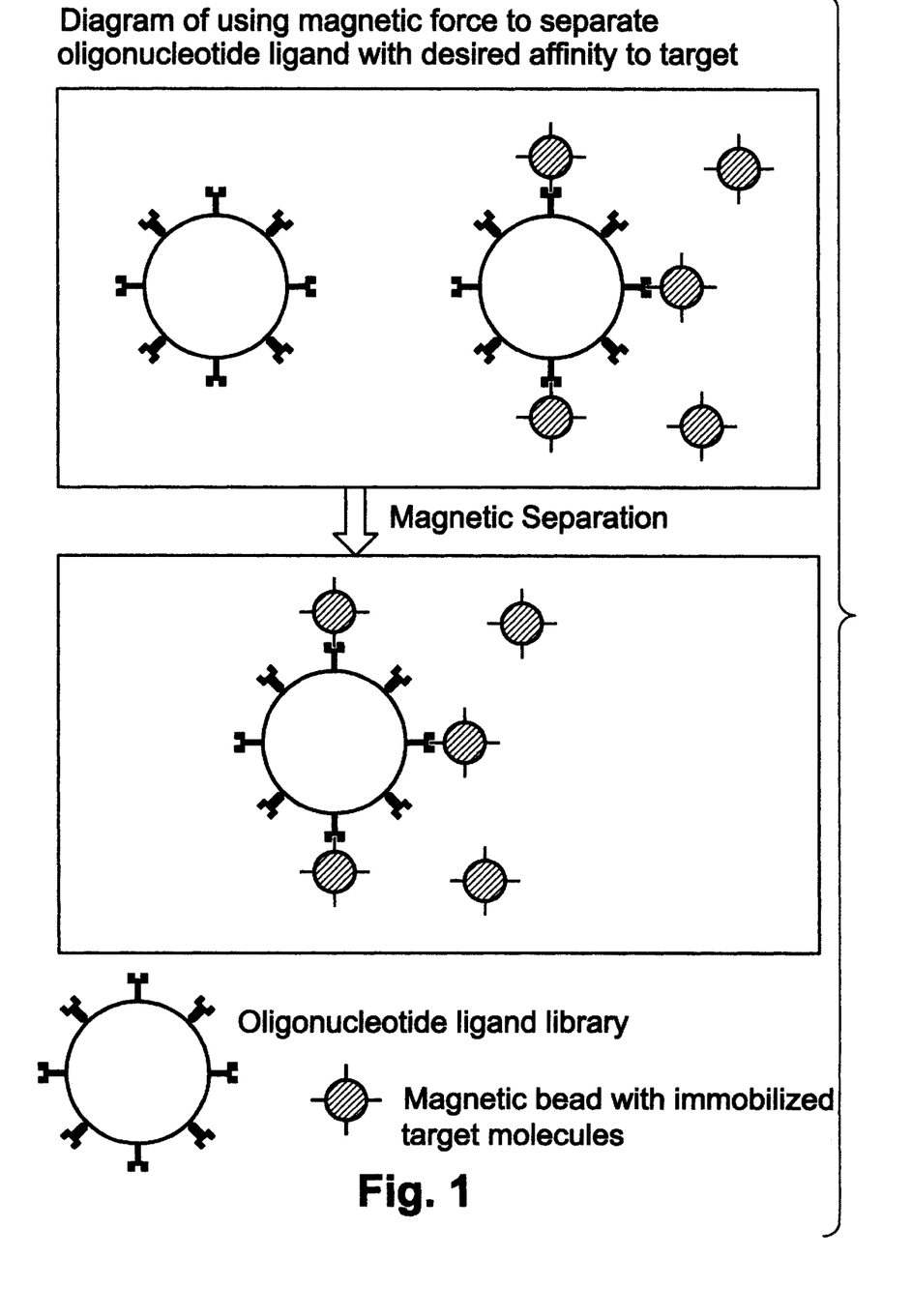
FIG. 1 is a schematic diagram showing a method of identifying oligonucleotide aptamers that uses magnetic separation.

FIG. 1 illustrates a process of selecting aptamers by magnetic separation. In this method, an oligonucleotide library is synthesized on TentaGel beads (polyethylene glycol grafted polystyrene-divinylbenzene polymer beads), each covered with a plurality of unique and identical oligonucleotides. The target molecule is linked (conjugated) to magnetic beads (Strepavidine-coated Dynal spheres M280). The diameter of resin beads for oligonucleotides is substantially larger than that of the magnetic beads (from about 10 to about 100 times larger). For example, the resin beads may have a diameter of about 90 m and are observable under an optical microscope, while the magnetic beads have a diameter of about 2.8 m.

The oligonucleotide library is brought into contact with the target molecule at a concentration preferably below the desired affinity. For example, if affinity of $10^{-6}$ M or higher is desired, the concentration of the target molecule is preferably below $10^{-6}$ M. The selection stringency can be adjusted by choosing the appropriate binding and washing conditions, and picking oligonucleotide beads above a defined fluorescence intensity. The selection stringency can be manipulated with salt concentrations between 50 mM and 250 mM NaCl, preferably between 100 mM and 200 mM NaCl.

After allowing the oligonucleotide library to interact with the target molecule-magnetic conjugate, magnetic force is applied to the mixture to separate complexed oligonucleotide resin beads from uncomplexed resin beads. The mixture in a microfuge tube is subject to a magnetic field and magnetic beads are retained on the side of the tube while non-magnetic beads can be washed away with buffers. The washing procedure is repeated several times and more stringent conditions can be applied to select for high affinity beads. The retained beads are examined, e.g., using fluorescence microscopy when the target molecules are fluor-labeled. Individual oligonucleotide resin beads can then be singled out and subject to sequencing and/or amplification.

2. Selecting Aptamers Using Flow Cytometry (1)

Figure 2:
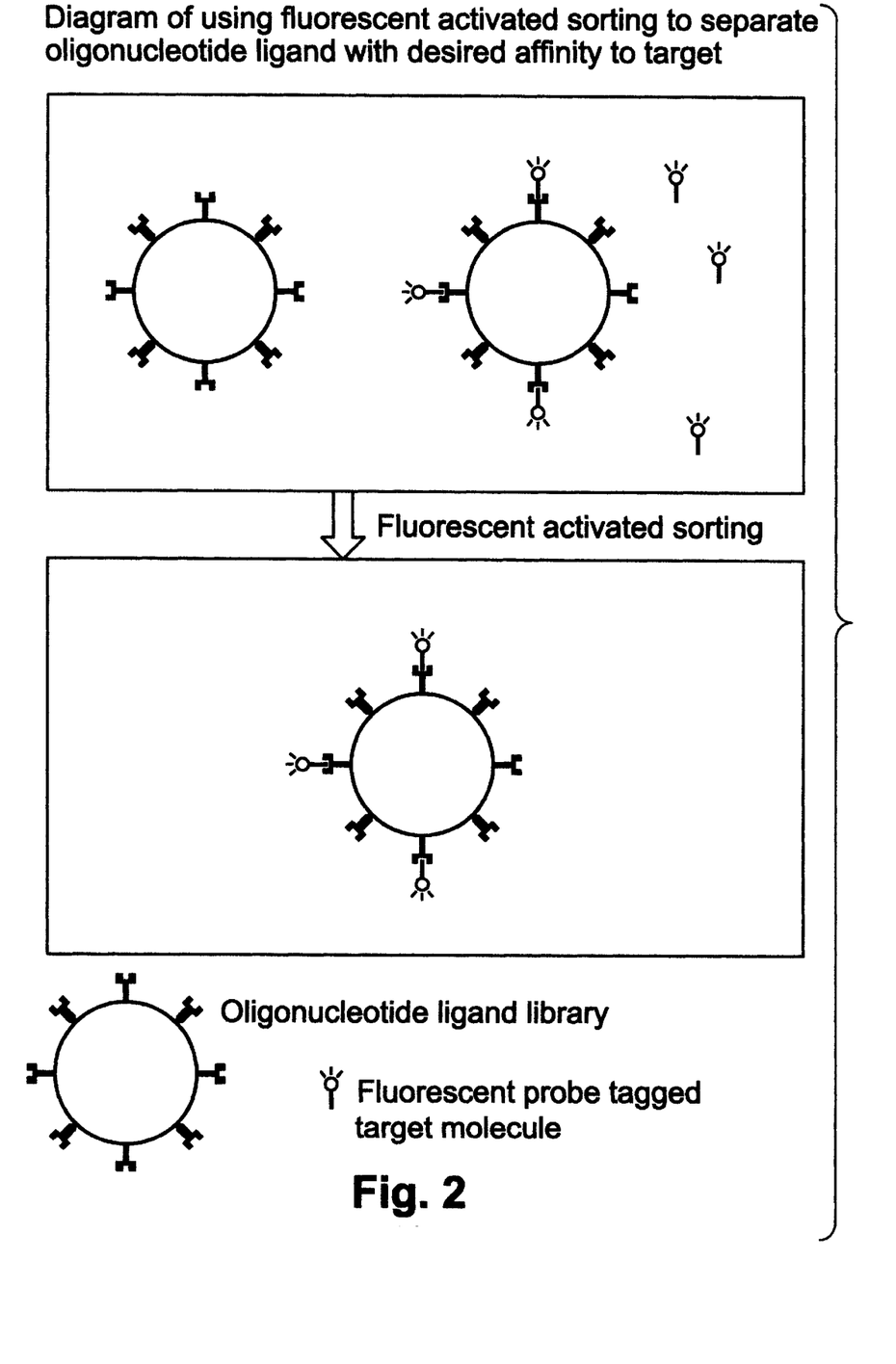
FIG. 2 is a schematic diagram showing a method of identifying oligonucleotide aptamers that uses fluorescence activated sorting.

FIG. 2 illustrates a process of selecting aptamers by fluorescence-activated sorting. In this method, an oligonucleotide library is synthesized on resin beads. The target molecule is conjugated with a fluorescent label.

The oligonucleotide library is brought into contact with the target molecule under conditions suitable for binding. The selection stringency can be adjusted by choosing the appropriate binding and washing conditions.

After allowing the oligonucleotide library to interact with the target molecule, the mixture is supplied to a FACS machine to select oligonucleotide resin beads bearing fluorescent label. oligonucleotide resin beads of varying fluorescence intensity can be separated automatically by programming the FACS machine to collect beads of specific fluorescence intensity in individual sample containers.

In a preferred embodiment, the target molecule:ligand complex is therefore marked and identified using both a fluorescent label and a magnetic label. After allowing the oligonucleotide library to interact with the target molecule, oligonucleotide aptamers for the target molecule are selected by magnetic force and sorted using fluorescence activated sorting.

3. Selecting Aptamers by Flow Cytometry (2)

Figure 3:
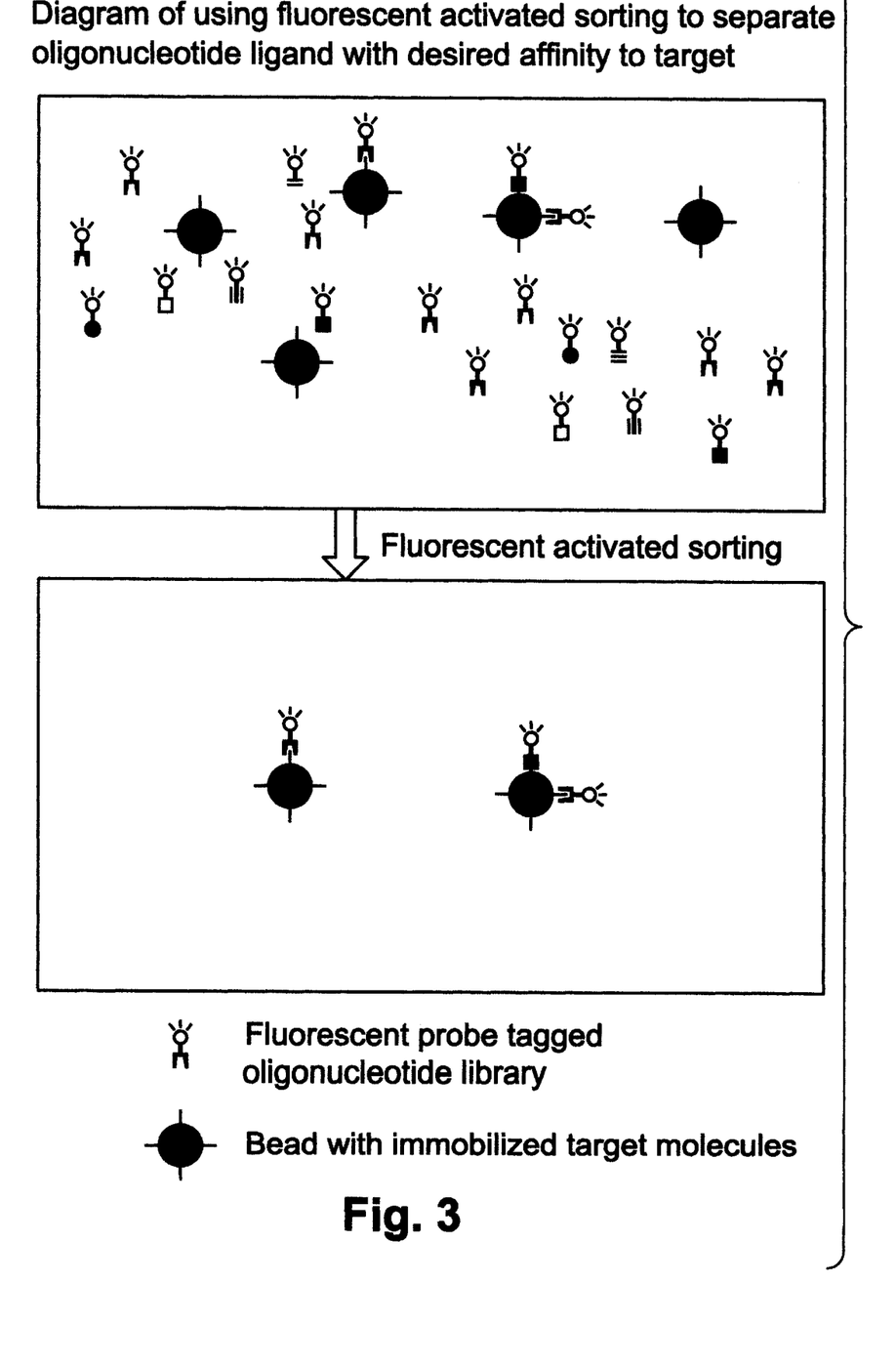
FIG. 3 is a schematic diagram showing another method of identifying oligonucleotide aptamers that uses fluorescence activated sorting.

FIG. 3 illustrates a second process of selecting aptamers by fluorescence activated sorting. In this method, a soluble oligonucleotide library is synthesized and each oligonucleotide is marked with a fluorescent label. The target molecule is linked to a solid support such as a bead.

The oligonucleotide library is brought into contact with the target molecule under conditions suitable for binding. The selection stringency can be adjusted by choosing the appropriate binding and washing conditions.

After allowing the oligonucleotide library to interact with the target molecule, the mixture is supplied to a FACS machine to select target molecule beads covered with fluorescent label.

4. Preparing a Library of Oligonucleotide Ligands

An oligonucleotide in a candidate library of this invention contains a variable region flanked by one or two constant regions. The variable region contains randomized sequences while the constant region(s) contains primer binding sites for amplification and/or sequencing of the oligonucleotide aptamer, and/or restriction sites for cloning. The variable region is designed to contain molecular diversity from which specific ligands can be selected.

In a preferred embodiment, an oligonucleotide library is prepared on solid support such as PEG resin beads. Each oligonucleotide is covalently linked to the resin. The molecular diversity is generated by split-pool strategy commonly practiced in combinatorial chemistry processes (Gallo et al., (1994) *J. Medicinal Chem.* 37:1233–1251). Oligonucleotides on each individual bead are preferably unique and identical. The oligonucleotide library therefore comprises a plurality of beads each representing a unique oligonucleotide construct. The size of a library is correlated to the complexity of oligonucleotide ligands. For example, $4^{13}$ (i.e., 67 million) individual beads are required for a 13 mer library which is completely randomized and representative. $4^{15}$ (i.e., 1 billion) beads are required for a 15 mer library which is completely randomized and representative.

The oligonucleotide can be DNA, RNA, their derivatives, mimetics, or a combination thereof.

In another preferred embodiment, the oligonucleotide or the solid support thereof is tagged with a marker, e.g., a fluorescent label which allows selection, e.g., by fluorescence activated sorting (FACS).

In yet another preferred embodiment, a soluble oligonucleotide library is synthesized with each oligonucleotide marked with a fluorescent label.

5. Preparing the Target Molecule for the Selection Process

A target molecule can be linked to a solid support such as a magnetic bead, either directly by covalent bonding or indirectly through a linker or precoated molecule such as a strepavidin coated bead. For example, erythropoietin molecules can be biotinylated with NHS-biotin and linked to strepavidin coated magnetic beads.

Alternatively, the target molecule can be labeled with a fluorescent probe such as fluorescein to allow selection by fluorescence activated sorting (FACS).

6. Amplifying and Sequencing the Selected Ligands

The selected oligonucleotides can be amplified with polymerase chain reactions utilizing primers directed to the constant regions of the oligonucleotides. The PCR products can be cloned and sequenced subsequently. Preferably, individual beads are sequenced directly with labeled primers, either manually or automatically.

Utility

The ligands isolated by the method of this invention can be used as affinity ligands to separate and purify target molecules, as probes to trace, monitor, detect and quantitate target molecules, or to block, activate or catalyze reactions that are physiologically relevant to achieve therapeutic effect (see review by Gold (1995) *J. Biol. Chem.* 270:13581–4).

Oligonucleotide ligands so isolated have utilities similar to antibodies. They can act as a pharmaceutical agent. They can bind to a specific target and direct specific molecules to a desired site, and/or they can inhibit or promote a physiologically relevant reaction to achieve a desired therapeutic effect. Various in vivo, ex vivo, and in vitro methods can employ the principles taught herein, as will appreciated by one of skill in the art.

Within respect to in vitro procedures, the applicant has found that isolated oligonucleotide aptamers can be used in affinity purification matrixes to purify target molecules. oligonucleotide aptamers are ideal for chromatographic separations of target molecules from contaminants. In a preferred embodiment, applicant has found that oligonucleotide aptamers are particularly useful for purifying target protein molecules from cell cultures or cell extracts.

Specifically, applicant has demonstrated a one step purification of prothrombin from crude plasma. The immediate application of this technology is to purify antibodies, enzymes, hormones, receptors, and factors that are used in research, development, diagnostic, pharmaceutical, industry applications.

Oligonucleotides of specific chiral properties can be used to separate chiral compounds and obtain optically pure chemicals.

Oligonucleotide ligands can also be used in place of antibodies in various research, development and diagnostic applications such as blotting techniques, flow cytometry, immunoassays, strip assays, immunohistological techniques, affinity sensors, etc. Oligonucleotide can further be used to monitor, trace, detect and quantitative desired target such as proteins, antibodies, microbes, virus, bacteria, macromolecules, and small molecules. Oligonucleotide ligands will also be valuable tools for proteomics studies of protein and their function.

EXAMPLE 1

Isolating Oligonucleotide Ligands for Erythropoietin

Synthesizing a Soluble Oligonucleotide Library

Deoxyoligonucleotides each containing 40 bases of random sequence flanked by two 18 base primer binding sites and a 5' fluorescein label were synthesized using standard techniques (Genosys). The 76 mer library has the following formula: 5'-F-label-CATGA ACTAG TGGAT CCG-40nt-TTGGT ACCCA ATTCG CCC-3' (seq ID NO: 1).

The 5' end constant region is comprised of 5'-CATGA ACTAG TGGAT CCG-3' (seq ID NO: 2), while the 3' end constant region is comprised of 5'-GGGCG AATTG GGTAC CAA-3' (seq ID NO: 3).

Restriction sites BamHI and Kpn I are designed into the constant regions to facilitate cloning and the production of probes.

Immobilizing EPO to Streptavidin Beads

Purified erythropoietin in 100 mM sodium bicarbonate buffer (pH 8.0) was biotinylated with NHS-biotin (molar ratio biotin:target 35:1, Calbiochem) for four hours at room temperature. Free biotin was removed by dialyzing against phosphate buffered saline. Biotinylated erythropoietin was linked to streptavidin beads (M280, Dynal) by incubating at 4° C. overnight.

Isolating Erythropoietin Binding Oligonucleotide Aptamers

The fluorescein tagged oligonucleotide library (119 nmol, contains $7 \times 10^{16}$ molecular diversity) was dissolved in PBS and incubated with erythropoietin immobilized on Dynal beads at room temperature for 15 minutes. The beads were washed with PBS five times and subject to fluorescence activated cell sorting (Becton-Dickson, FACStar Plus). Beads with the highest fluorescent intensity (0.1% of the total 600,000 beads scanned) were collected in PBS and subject to polymerase chain reaction (PCR) with Taq polymerase (Life Technologies). A total of twenty-five to thirty cycles were performed on a Perkin-Elmer DNA Thermal cycler (denaturing at 94° C. for 45 sec, annealing at 60° C. for 45 sec, and chain extension at 72° C. for 1 minute) The PCR products were verified on 2% agarose TBE electrophoresis and digested with restriction enzymes Kpn 1 and BamH1 (New England Biolabs). The digested fragments were ligated and cloned into vector pBlueScript KS (Stratagene) and transformed into bacterial host DH5α. Individual colonies were identified.

Testing the Affinity of an Aptamer to Erythropoietin

Plasmid DNA was prepared using boiling miniprep procedures according to Sambrook, Fritsch and Maniatis, *Molecular Cloning: A Laboratory Manual*, Second Edition (1989). Plasmids were digested with Kpn I and BamHI, and the fragments were end-labeled using $^{32}$P-ATP and kinase. After the restriction digestion, the sense strand contains protruding ends 8 bases longer than the antisense strand. The labeled fragment were then denatured by sequencing stop buffer and heated at 100° C. for 2 min, and electrophoretically separated on a 15% urea-TBE polyacrylamide gel.

Single stranded radioactive $^{32}$p labeled probes were excised from the gel and eluted in 0.5 M NaAc, 20 mM Tris, pH 7.5, 10 mM EDTA, 0.1% SDS at 65° C. for 30 min. The probes were then extracted with phenol, precipitated with tRNA and ethanol, and air dried.

The probes were dissolved in PBS. Binding assays were performed in PBS at room temperature for 15 min. The formed complexes were electrophoretically resolved in a native 0.5× TBE 4% polyacrylamide gel, and then exposed on X-ray film (Kodak).

Erythropoietin-bound aptamers were identified thereby and sequenced using the following primers:

Sense primer (Seq ID NO: 4)
5'-AGCGGATAACAATTTCACACAGGA-3'

Antisense primer (Seq ID NO: 5)
5'-CGCCAGGGTTTTCCCAGTCACGAC-3'

Manual sequencing was performed according to the manufacturer's instructions (Amersham USB).

A consensus sequence emerged from five sequenced aptamers as shown in FIG. 4, Group I. This consensus sequence was found to bind erythropoietin, albeit with slightly lower affinity than the five aptamers identified. Three other aptamers were found that shared no homology with the consensus sequence (FIG. 4, Group II).

The minimal consensus sequence and constructs bearing several copies of consensus demonstrated more or less binding. The spaced region between the two consensus sequences was found to affect binding ability. It was thus determined that oligonucleotides with more or less affinity for the target molecule of interest could be prepared and identified based on the consensus sequence.

The specificity of oligonucleotide ligand to EPO is demonstrated in FIG. 2 by its ability to bind to EPO and not an equi-molar amount of bovine serum albumin.

EXAMPLE 2

Purification of Prothrombin with an Oligonucleotide Ligand Matrix

Oligonucleotide ligand against thrombin has been isolated by Bock et al., *Nature* 355:584–566, 1992. The converse utility of an oligonucleotide ligand as affinity matrix to purify protein from crude extracts is demonstrated by the following.

Biotinylated oligonucleotide ligand against thrombin is produced according to known procedures (e.g., Genosys). The sequence (Seq ID NO: 6) of the ligand is as follows:

5'-GGTTGGTGTG GTTGGATGAT GGTTGGTGTG GTTGGTAAGT-3'-biotin

The ligand (99 nmol) is labeled with T4 kinase with $^{32}$P-ATP (New England Biolabs). Free radioactivity is removed by passage through a sephadex G25 spin column. The labeled ligands were incubated with 0.5 ml streptavidin-agarose (Life Technologies) at 4° C. overnight. Coupling efficiency is monitored by reduced radioactivity in the solution before and after incubation. Coupling efficiency was found to be 71%.

The matrix bound ligand is packed in a small column (BioRad) and washed with phosphate buffered saline. Human plasma (Calbiochem, 10 ml) is loaded on the column. After washing with PBS, the bound prothrombin is eluted with 1 M NaCl, 5 mM EDTA, 25 mM Tris, pH 7.4.

The collected sample is analyzed by 7.5% SDS-PAGE, shown in FIG. 3A and identity of prothrombin verified by western blotting as shown in FIG. 3B.

Alternatively, the ligand can be synthesized directly on a solid support, preferably polyethylene glycol grafted polystyrene beads or cellulose based membrane.

EXAMPLE 3

Synthesis of Oligonucleotide Library on Solid Support

PEG-grafted polystyrene beads (TentaGel S) are purchased from Fluka. Loading is controlled by reacting the beads with defined amount of DMT-Cl and capping the remaining OH groups on the support. The oligonucleotides are synthesized on an ABI 394 DNA synthesizer using standard procedures. One gram of solid support is divided into four equal parts and synthesis performed in four columns. After the primer synthesis, the supports are mixed together and divided into four equal parts again and an additional base synthesized. The mix-split process is repeated for synthesis of a total of 20 bases, each column having a defined base for each of the 20 rounds. After the mix-split, the second primer is synthesized.

Synthesis is monitored by trityl efficiency and the polymerase chain reaction.

All publications noted, none of which is admitted prior art, are incorporated herein by reference, including nucleic acid and amino acid sequence listings.

One of skill in the art will appreciate that other aspects and embodiments are possible within the true scope and spirit of the imvention. The claims below are further illustrative.

What is claimed is:

1. A method for identifying an aptamer which specifically binds to a target molecule other than a nucleic acid, comprising the steps of:
   a) providing a collection of oligonucleotides attached to a plurality of solid supports, wherein oligonucleotides of different nucleotide sequences are attached to different solid supports and all oligonucleotides attached to a single solid support are of the same nucleotide sequence;
   b) providing a plurality of magnetic beads having said target molecule immobilized on their surface;
   c) admixing said collection of oligonucleotides with said plurality of magnetic beads under conditions wherein the oligonucleotide ligands become bound to the target molecule;
   d) applying magnetic force to isolate one or more solid supports bound to magnetic beads; and
   e) identifying oligonucleotides attached to said one or more isolated solid supports.

2. The method of claim 1, wherein said solid supports are resin beads and said step d) comprises selecting resin beads bound to magnetic beads.

3. The method of claim 2, wherein said resin beads have a diameter of about 50 um to about 500 um.

4. The method of claim 2, wherein said resin beads have a diameter of about 70 um to about 150 um.

5. The method of claim 2, wherein said resin beads have a diameter of about 90 um to about 120 um.

6. The method of claim 1, wherein said magnetic beads have a diameter of about 1 um to about 10 um.

7. The method of claim 1, wherein said magnetic beads have a diameter of about 2 um to about 5 um.

8. The method of claim 1, wherein said target molecule is labeled with a fluorescent probe.

9. The method of claim 1, wherein said collection of oligonucleotides are synthesized on said plurality of solid supports.

10. A method for identifying an aptamer which specifically binds to a target molecule other than a nucleic acid, comprising the steps of:
   a) providing a collection of oligonucleotides attached to a plurality of solid supports, wherein oligonucleotides of different nucleotide sequences are attached to different solid supports and all oligonucleotides attached to a single solid support are of the same nucleotide sequence;
   b) providing a plurality of said target molecules labeled with fluorescent probe and linked to a plurality of solid supports;
   c) admixing said collection of oligonucleotides with said plurality of said target molecules under conditions wherein the oligonucleotide ligands become bound to target molecule;
   d) isolating one or more solid supports attached with fluorescent probe; and
   e) identifying oligonucleotides attached to said one or more isolated solid supports.

11. The method of claim 10, wherein said fluorescence labeled target molecules are linked to magetic beads.

12. The method of claim 11, further comprising the step of applying magnetic force to isolate solid supports attached to oligonucleotides bound to said target molecules linked to magnetic beads after step c) and before step d).

13. A method for identifying an aptamer which specifically binds to a target molecule other than a nucleic acid, comprising the steps of:
   a) providing a collection of fluorescence labeled oligonucleotides of different nucleotide sequences attached to a plurality of solid supports;
   b) providing a plurality of solid supports having said target molecule immobilized on their surface;
   c) admixing said collection of oligonucleotides with said plurality of solid supports under conditions wherein the oligonucleotide ligands become bound to the target molecule;
   d) isolating solid supports attached with fluorescence labeled oligonucleotides; and
   e) identifying oligonucleotides attached to said isolated solid supports.

* * * * *

SEQUENCE LISTING

<160> NUMBER OF SEQ ID NOS: 15

<210> SEQ ID NO 1
<211> LENGTH: 76
<212> TYPE: DNA
<213> ORGANISM: Artificial Sequence
<220> FEATURE:
<223> OTHER INFORMATION: Synthesized Deoxyoligonucleotide.
<220> FEATURE:
<223> OTHER INFORMATION: Library of synthetic nucleotide sequences
      varying only at the "n" position; "n" stands for any base.

<400> SEQUENCE: 1
catgaactag tggatccgnn nnnnnnnnnn nnnnnnnnnn nnnnnnnnnn nnnnnnnntt     60
ggtacccaat tcgccc                                                    76

<210> SEQ ID NO 2
<211> LENGTH: 18
<212> TYPE: DNA
<213> ORGANISM: Artificial Sequence
<220> FEATURE:
<223> OTHER INFORMATION: Synthesized deoxyoligonucleotide.

<400> SEQUENCE: 2
catgaactag tggatccg                                                  18

<210> SEQ ID NO 3
<211> LENGTH: 18
<212> TYPE: DNA
<213> ORGANISM: Artificial Sequence
<220> FEATURE:
<223> OTHER INFORMATION: Synthesized deoxyoligonucleotide.

<400> SEQUENCE: 3
gggcgaattg ggtaccaa                                                  18

<210> SEQ ID NO 4
<211> LENGTH: 24
<212> TYPE: DNA
<213> ORGANISM: Artificial Sequence
<220> FEATURE:
<223> OTHER INFORMATION: Synthesized deoxyoligonucleotide.

<400> SEQUENCE: 4
agcggataac aatttcacac agga                                           24

<210> SEQ ID NO 5
<211> LENGTH: 24
<212> TYPE: DNA
<213> ORGANISM: Artificial Sequence
<220> FEATURE:
<223> OTHER INFORMATION: Synthesized deoxyoligonucleotide.

<400> SEQUENCE: 5
cgccagggtt ttcccagtca cgac                                           24

<210> SEQ ID NO 6
<211> LENGTH: 40
<212> TYPE: DNA
<213> ORGANISM: Artificial Sequence
<220> FEATURE:
<223> OTHER INFORMATION: Synthesized oligonucleotide biotinylated at
      the 3' "t".

<400> SEQUENCE: 6

```
ggttggtgtg gttggatgat ggttggtgtg gttggtaagt                            40
```

<210> SEQ ID NO 7
<211> LENGTH: 8
<212> TYPE: DNA
<213> ORGANISM: Artificial Sequence
<220> FEATURE:
<223> OTHER INFORMATION: Putative consensus sequence in group of
      aptamers having affinity for human erythropoietin.

<400> SEQUENCE: 7

```
tgtttgtt                                                               8
```

<210> SEQ ID NO 8
<211> LENGTH: 45
<212> TYPE: DNA
<213> ORGANISM: Artificial Sequence
<220> FEATURE:
<223> OTHER INFORMATION: Synthetic aptamers having affinity for human
      erythropoietin.

<400> SEQUENCE: 8

```
ggccatcgtt cctgttcctt atcttcaata cgctgccgcg acctt                      45
```

<210> SEQ ID NO 9
<211> LENGTH: 44
<212> TYPE: DNA
<213> ORGANISM: Artificial Sequence
<220> FEATURE:
<223> OTHER INFORMATION: Synthetic aptamers having affinity for human
      erythropoietin.

<400> SEQUENCE: 9

```
gggggccaag gattcatgtg tttgtttaac agctagcgcc gctt                       44
```

<210> SEQ ID NO 10
<211> LENGTH: 43
<212> TYPE: DNA
<213> ORGANISM: Artificial Sequence
<220> FEATURE:
<223> OTHER INFORMATION: Synthetic aptamers having affinity for human
      erythropoietin.

<400> SEQUENCE: 10

```
gggacctccc agaagcgaag gtgttcaacg ttggtttagg ttt                        43
```

<210> SEQ ID NO 11
<211> LENGTH: 42
<212> TYPE: DNA
<213> ORGANISM: Artificial Sequence
<220> FEATURE:
<223> OTHER INFORMATION: Synthetic aptamers having affinity for human
      erythropoietin.

<400> SEQUENCE: 11

```
gggacaaggt tgtaggcttc agtgtctctg ttcgtgttgg tt                         42
```

<210> SEQ ID NO 12
<211> LENGTH: 43
<212> TYPE: DNA
<213> ORGANISM: Artificial Sequence
<220> FEATURE:
<223> OTHER INFORMATION: Synthetic aptamers having affinity for human
      erythropoietin.

<400> SEQUENCE: 12

-continued

```
ggcgatacgg aatattggta ccacctatgt gtagatgttt gtt                43
```

<210> SEQ ID NO 13
<211> LENGTH: 43
<212> TYPE: DNA
<213> ORGANISM: Artificial Sequence
<220> FEATURE:
<223> OTHER INFORMATION: Synthetic aptamers having affinity for human erythropoietin.

<400> SEQUENCE: 13

```
ggcccggtgg tgagatcaga gttagtgagt tcttctgtcc gtt                43
```

<210> SEQ ID NO 14
<211> LENGTH: 45
<212> TYPE: DNA
<213> ORGANISM: Artificial Sequence
<220> FEATURE:
<223> OTHER INFORMATION: Synthetic aptamers having affinity for human erythropoietin.

<400> SEQUENCE: 14

```
gggagccgaa tgtatgaaag tgctgagtac aggtgctcgg gggtt              45
```

<210> SEQ ID NO 15
<211> LENGTH: 43
<212> TYPE: DNA
<213> ORGANISM: Artificial Sequence
<220> FEATURE:
<223> OTHER INFORMATION: Synthetic aptamers having affinity for human erythropoietin.

<400> SEQUENCE: 15

```
ggggcagggg cggacgacgg ctagtgcaga cttttggtgg gtt                43
```